(12) United States Patent
Mashiach

(10) Patent No.: US 10,806,926 B2
(45) Date of Patent: Oct. 20, 2020

(54) IMPLANTABLE ELECTRICAL STIMULATOR

(75) Inventor: Adi Mashiach, Tel Aviv (IL)

(73) Assignee: MAN & SCIENCE SA, Mont-St-Guibert (BE)

( * ) Notice: Subject to any disclaimer, the term of this patent is extended or adjusted under 35 U.S.C. 154(b) by 0 days.

(21) Appl. No.: 12/581,907

(22) Filed: Oct. 20, 2009

(65) Prior Publication Data

US 2011/0093036 A1    Apr. 21, 2011

(51) Int. Cl.
*A61N 1/36* (2006.01)
*A61N 1/05* (2006.01)
*A61N 1/375* (2006.01)

(52) U.S. Cl.
CPC .......... *A61N 1/3601* (2013.01); *A61N 1/05* (2013.01); *A61N 1/0553* (2013.01); *A61N 1/3756* (2013.01)

(58) Field of Classification Search
CPC . A61N 1/3787; A61N 1/37205; A61N 1/3601
USPC .................................. 607/1, 48, 59
See application file for complete search history.

(56) References Cited

U.S. PATENT DOCUMENTS

| | | |
|---|---|---|
| 4,837,049 A | 6/1989 | Byers et al. |
| 5,174,287 A | 12/1992 | Kallok et al. |
| 5,485,851 A | 1/1996 | Erickson |
| 5,540,733 A | 7/1996 | Testerman et al. |
| 6,038,480 A | 3/2000 | Hrdlicka et al. |
| 6,051,017 A | 4/2000 | Loeb et al. |
| 6,240,316 B1 | 5/2001 | Richmond et al. |
| 6,275,737 B1 | 8/2001 | Mann |
| 6,345,202 B2 | 2/2002 | Richmond et al. |
| 6,393,325 B1 * | 5/2002 | Mann ................ A61N 1/36071 607/46 |
| 6,587,725 B1 | 7/2003 | Durand et al. |
| 6,625,494 B2 | 9/2003 | Fang et al. |
| 6,636,767 B1 | 10/2003 | Knudson et al. |
| 7,272,443 B2 | 9/2007 | Min et al. |
| 7,277,749 B2 | 10/2007 | Gordon et al. |
| 7,447,551 B2 | 11/2008 | Kuo et al. |
| 7,680,538 B2 | 3/2010 | Durant et al. |
| 7,725,195 B2 | 5/2010 | Lima et al. |
| 7,809,442 B2 | 10/2010 | Bolea et al. |
| 2001/0018547 A1 * | 8/2001 | Mechlenburg et al. ........ 600/15 |
| 2004/0059392 A1 | 3/2004 | Parramon et al. |

(Continued)

FOREIGN PATENT DOCUMENTS

| | | |
|---|---|---|
| WO | WO 2007/098200 | 8/2007 |
| WO | WO 2007/098202 | 8/2007 |
| WO | WO 2011/077433 | 6/2011 |

OTHER PUBLICATIONS

Brindley, G.S., Transmission of electrical stimuli along many independent channels through a fairly small area of intact skin, Proceedings of the Physiological Society, Dec. 1964, pp. 44-46.

(Continued)

*Primary Examiner* — Michael J D Abreu
(74) *Attorney, Agent, or Firm* — Finnegan, Henderson, Farabow, Garrett & Dunner, LLP

(57) ABSTRACT

An implantable stimulator for stimulating muscles or nerves, including, an array of electrodes for electrically stimulating muscles or nerves, a controller for controlling the activity of the electrodes, and wherein the controller is adapted to dynamically select the electrodes that are used to participate in stimulating the muscles or nerves.

10 Claims, 5 Drawing Sheets

(56) References Cited

U.S. PATENT DOCUMENTS

| | | | |
|---|---|---|---|
| 2004/0153127 A1* | 8/2004 | Gordon et al. | 607/1 |
| 2004/0172089 A1 | 9/2004 | Whitehurst et al. | |
| 2005/0010265 A1 | 1/2005 | Baru Fassio et al. | |
| 2005/0043772 A1 | 2/2005 | Stahmann et al. | |
| 2005/0070971 A1 | 3/2005 | Fowler et al. | |
| 2005/0187584 A1* | 8/2005 | Denker | A61N 1/36114 607/5 |
| 2007/0073357 A1 | 3/2007 | Rooney et al. | |
| 2007/0173893 A1 | 7/2007 | Pitts | |
| 2008/0021506 A1 | 1/2008 | Grocela | |
| 2008/0027503 A1 | 1/2008 | Marrosu et al. | |
| 2008/0041398 A1 | 2/2008 | Hegde et al. | |
| 2008/0064946 A1 | 3/2008 | Greenberg et al. | |
| 2008/0103407 A1* | 5/2008 | Bolea | A61N 1/3606 600/529 |
| 2008/0109046 A1 | 5/2008 | Lima et al. | |
| 2008/0132962 A1 | 6/2008 | DiUbaldi et al. | |
| 2008/0147141 A1 | 6/2008 | Testerman et al. | |
| 2009/0078274 A1 | 3/2009 | Bhat et al. | |
| 2010/0094379 A1 | 4/2010 | Meadows et al. | |
| 2010/0114190 A1 | 5/2010 | Bendett et al. | |
| 2010/0137948 A1* | 6/2010 | Aghassian | A61N 1/3787 607/61 |
| 2010/0191136 A1 | 7/2010 | Wolford | |
| 2010/0228313 A1 | 9/2010 | Starkebaum et al. | |
| 2010/0292527 A1 | 11/2010 | Schneider et al. | |
| 2011/0065979 A1 | 3/2011 | Lehrman et al. | |
| 2011/0071591 A1 | 3/2011 | Bolea et al. | |

OTHER PUBLICATIONS

Tran W.H., First Subject Evaluated with Simulated BION Treatment in Posterior Genioglossus to Prevent Obstructive Sleep Apnea, Proceedings of the 26$^{th}$ Annual International Conference of IEEE EMBS, Sep. 2004, pp. 4287-4289.

Schwartz, Alan R., Therapeutic Stimulation of the Hypoglossal Nerve in Obstructive Sleep Apnea, Archives of Otolaryngology Head and Neck Surgery, vol. 127, Oct. 2001, pp. 1216-1223.

Eastwood, P.R., Treatment of Obstructive Sleep Apnea with Unilateral Hypoglossal Nerve Stimulation, American Journal of Respiratory Critical Care Medicine, vol. 181, May 2010. pp. 5393-5394.

Eisele, David W., Tongue neuromuscular and direct hypoglossal nerve stimulation for obstructive sleep apnea, Otolaryngologic Clinics of North America, Jun. 2003, pp. 501-510.

Examination Report for Australian Patent Application No. 2010309433, dated Sep. 17, 2015 (3 pgs.).

Notice of Acceptance for Australian Patent Application No. 2010309433, dated Oct. 7, 2015 (2 pgs.).

EPC Communication received from European Patent Office for European Application No. 10 781 533.4, dated Nov. 24, 2016, 4 pages.

* cited by examiner

IMPLANTABLE ELECTRICAL STIMULATOR

FIELD OF THE INVENTION

The present invention relates generally to an implantable electrical stimulator and more specifically to an implantable electrical stimulator with a dynamically controlled electrode array.

BACKGROUND OF THE INVENTION

Implanting a stimulator to stimulate muscles or nerves is a complex procedure. Generally in the case of nerve stimulation, a special electrode is used, such as a cuff electrode. Generally the electrode is in the form of a wire extending from the stimulator to the nerve. Implantation of the stimulator requires surgical intervention to expose the position for implanting the electrode and stimulator and then requires fine-tuning the placement of the electrode so that accurate contact will be formed between the electrodes of the stimulator and specific contact points along the muscles or nerves.

In the case of muscle stimulators, the electrodes are typically positioned to form contact with the motor end plate of a muscle, also called the neuromuscular junction of the muscle. In most muscles the motor end plate is located in the middle of the muscle, where the motor neuron interfaces with the muscle.

In recent years manufactures have managed to reduce the size of stimulators significantly, for example to approximately 3 mm by 27 mm. In a reduced size stimulator the electrode may be provided as a rigid metal contact extending from the body of the stimulator and the stimulator is implanted with the electrode positioned in contact with the muscle/nerve contact points.

One method to achieve the correct positioning is by trial and error, wherein the practitioner inserts the stimulator to a selected position and then provides a charge to the electrodes of the stimulator to verify the position according to the response of the muscles, for example contraction of the entire muscle indicates a successful positioning and local contraction indicates an unsuccessful positioning. This method requires a high level of expertise from the practitioner and may be very time consuming.

Another method suggests the use of a probe that also serves as the introduction device for the stimulator. The practitioner uses the probe to locate the desired position and then uses the probe to insert the stimulator to the located position.

Some problems may occur after positioning the stimulator. One problem is that a rigid stimulator may damage the muscles/nerves or surrounding tissue and lead to complications, for example causing inflammation, which may reduce tissue conductivity, so that the stimulator device may not stimulate the muscles/nerves properly. A second problem that may occur is movement of the stimulator and/or electrodes, which may cause a shift in the electrode alignment. The shift in the electrode alignment may reduce stimulation of the muscles/nerves thus preventing the stimulator from effectively causing tissue stimulation.

U.S. Pat. No. 7,447,551 to Kuo et al. the disclosure of which is incorporated herein by reference describes using a flexible circuit board in creating an implantable stimulator. The stimulator is coated with a flexible bio-compatible package material to enhance safety, durability and reliability of the implantable stimulator. Kuo further discloses using an array of electrodes to enlarge the electrical treatment area and improving the electrical treatment efficiency.

SUMMARY OF THE INVENTION

An aspect of an embodiment of the invention, relates to an implantable stimulator for stimulating muscles and/or nerves, with a dynamically controllable array of electrodes. The array of electrodes is made up from one or more rows and one or more columns of electrodes positioned on a surface that can be placed in contact with a muscle/nerve. Optionally, the stimulator may have multiple arrays, for example one on each side of the stimulator or even multiple arrays on each side of the stimulator. In an exemplary embodiment of the invention, the array of electrodes has a density greater than the density of the muscle/nerve contact points, which need to be stimulated; or the array of electrodes occupies an area larger than that of the muscle/nerve contact point. In any of the above two options, once the stimulator is initially positioned at least some of the electrodes will coincide with the position of the contact points.

In an exemplary embodiment of the invention, the stimulator automatically determines which electrodes are in contact with points on the muscle/nerve wherein the action potentials signals measured at those points indicates that they are desirable contact points. The properties measured for an action potential signal may include among other details: frequency, amplitude, and propagation speed. Optionally, when relating to muscle stimulation, the contact points are generally located in the motor units, which include the neuromuscular junction.

In an exemplary embodiment of the invention, the method of selecting a specific electrode or group of electrodes may include measuring the action potentials amplitudes, and creating time integrals, for example by using Root Mean Square to determine the location of the muscle's Motor Units. Alternatively or additionally, other algorithms, such as decomposition algorithms, or Correlation Kernel Compensation, may help to determine the location of the muscle's Motor Units. Optionally, the electrodes that are close or in contact with the muscle's Motor Units are selected as having measured the lowest resistance at the electrode contact point and those electrodes are used to stimulate the muscles/nerves of the patient. Optionally, the determination may be made periodically or upon request of the patient or practitioner. In an alternative embodiment of the invention, the practitioner that installs the stimulator, communicates with the stimulator wirelessly using a computer and selects the electrodes that elicit the most prominent clinical reaction.

In an exemplary embodiment of the invention, the array of electrodes is used to identify contracting regions. The controller in the stimulator can then choose to stimulate the contracting regions or the non-contracting regions.

In some embodiments of the invention, the electrodes serve as inputs and outputs. Alternatively, some of the electrodes serve as inputs and some serve as outputs. Optionally, the inputs measure the resistance or electrical activity of the muscle/nerve at their contact point with the muscle/nerve.

In some embodiment of the invention, the stimulator is made up from a few basic rigid elements, for example an integrated circuit to control the stimulator, a memory chip, a power source (e.g. a battery), a transceiver and other elements. Optionally, each element is wrapped separately in a bio-compatible encasement and connected with flexible wiring or a common flexible backbone serving as a communication bus between the elements of the stimulator, thus providing a flexible stimulator. In an exemplary embodiment of the invention, the electrodes are provided as a separate element made up from an array of contacts on a flexible material, for example, wherein the material is made up from Polyimide, Polyester or PEEK thermoplastic with the electrodes embedded in it.

There is thus provided according to an exemplary embodiment of the invention, an implantable stimulator for stimulating muscles or nerves, including:

an array of electrodes for electrically stimulating muscles or nerves;

a controller for controlling the activity of the electrodes;

wherein the controller is adapted to dynamically select the electrodes that are used to participate in stimulating the muscles or nerves.

Optionally, the implantable stimulator further includes a power source to power the stimulator.

In an exemplary embodiment of the invention, the implantable stimulator further includes a transceiver to wirelessly communicate with external devices and receive commands for the controller.

Optionally, the controller selects the electrodes responsive to a communication from an external device.

In an exemplary embodiment of the invention, the controller periodically updates the selection of electrodes to participate in stimulation of the muscle or nerve.

Optionally, the controller selects the electrodes responsive to a determination made by electrical measurements made by the electrodes.

In an exemplary embodiment of the invention, substantially all the electrodes can serve as inputs to measure electrical activity in the muscles or nerves and as outputs to electrically stimulate the muscles or nerves.

Optionally, some of the electrodes serve as inputs to measure electrical activity in the muscles or nerves and some of the electrodes serve as outputs to electrically stimulate the muscles or nerves.

In an exemplary embodiment of the invention, the density of the array of electrodes is greater than the density of the active contact points of the muscle or nerve being stimulated by the stimulator.

Optionally, the array of electrodes is connected by flexible wires to the other elements of the stimulator.

In an exemplary embodiment of the invention, the stimulator is made up from multiple independent parts connected together electrically by a flexible connection.

Optionally, the stimulator is made up from flexible material.

In an exemplary embodiment of the invention, the array of electrodes forms a three-dimensional shape shielding the controller in said three-dimensional shape.

In an exemplary embodiment of the invention, the implantable stimulator further includes a housing, and said controller is located within the housing.

Optionally, the implantable stimulator further includes a housing, and the controller, and the power source are located within the housing.

In an exemplary embodiment of the invention, the stimulator is adapted to be implanted at the base of a person's tongue.

Optionally, the implantable stimulator further includes sensors to sense physiological parameters of the person with the implanted stimulator.

In an exemplary embodiment of the invention, the sensors are adapted to sense physical parameters from the group consisting of temperature, vibrations, and audio signals.

Optionally, the stimulator is activated responsive to measurements received by the sensors.

In an exemplary embodiment of the invention, the power source receives power wirelessly.

There is further provided according to an exemplary embodiment of the invention, a method of stimulating muscles or nerves using an implantable stimulator with an array of electrodes, including:

dynamically selecting the electrodes that will participate in stimulating the muscle or nerve from the available electrodes; and activating the selected electrodes to stimulate a muscle or nerve.

In an exemplary embodiment of the invention, the method further includes implanting the stimulator so that the array of electrodes is in proximity with a muscle or nerve.

Optionally, the selection is performed manually by a practitioner by communicating with the stimulator and instructing the stimulator to activate one or more electrodes or groups of electrodes while observing the response.

Alternatively or additionally, the selection is performed by the electrode array measuring electrical parameters through one or more electrodes or group of electrodes and making a selection based on the results of said measurements.

Optionally, the selection is performed by the electrode array measuring electrical parameters through an external device.

In an exemplary embodiment of the invention, the selection is repeated periodically.

Optionally, the selection is activated responsive to inputs accepted by the stimulator.

In an exemplary embodiment of the invention, the selection is activated responsive to sensor input.

Optionally, dynamically selecting further includes performing a pre-programmed algorithm to weigh the results from various inputs and determining whether to provide stimulation.

In an exemplary embodiment of the invention, the method further includes determining the specific stimulation protocol to provide.

Optionally, the dynamic selection is responsive to electrical measurements at the location of the electrodes.

In an exemplary embodiment of the invention, the dynamic selection is responsive to responsiveness of the nerve or muscle at the location of the electrodes.

Optionally, the method further includes adjusting the stimulator responsive to a measurement before activating the stimulator.

In an exemplary embodiment of the invention, the stimulation is provided at specific times, for specific time duration, or periodically.

BRIEF DESCRIPTION OF THE DRAWINGS

The present invention will be understood and better appreciated from the following detailed description taken in conjunction with the drawings. Identical structures, elements or parts, which appear in more than one figure, are generally labeled with the same or similar number in all the figures in which they appear, wherein.

DETAILED DESCRIPTION

Figure 1:
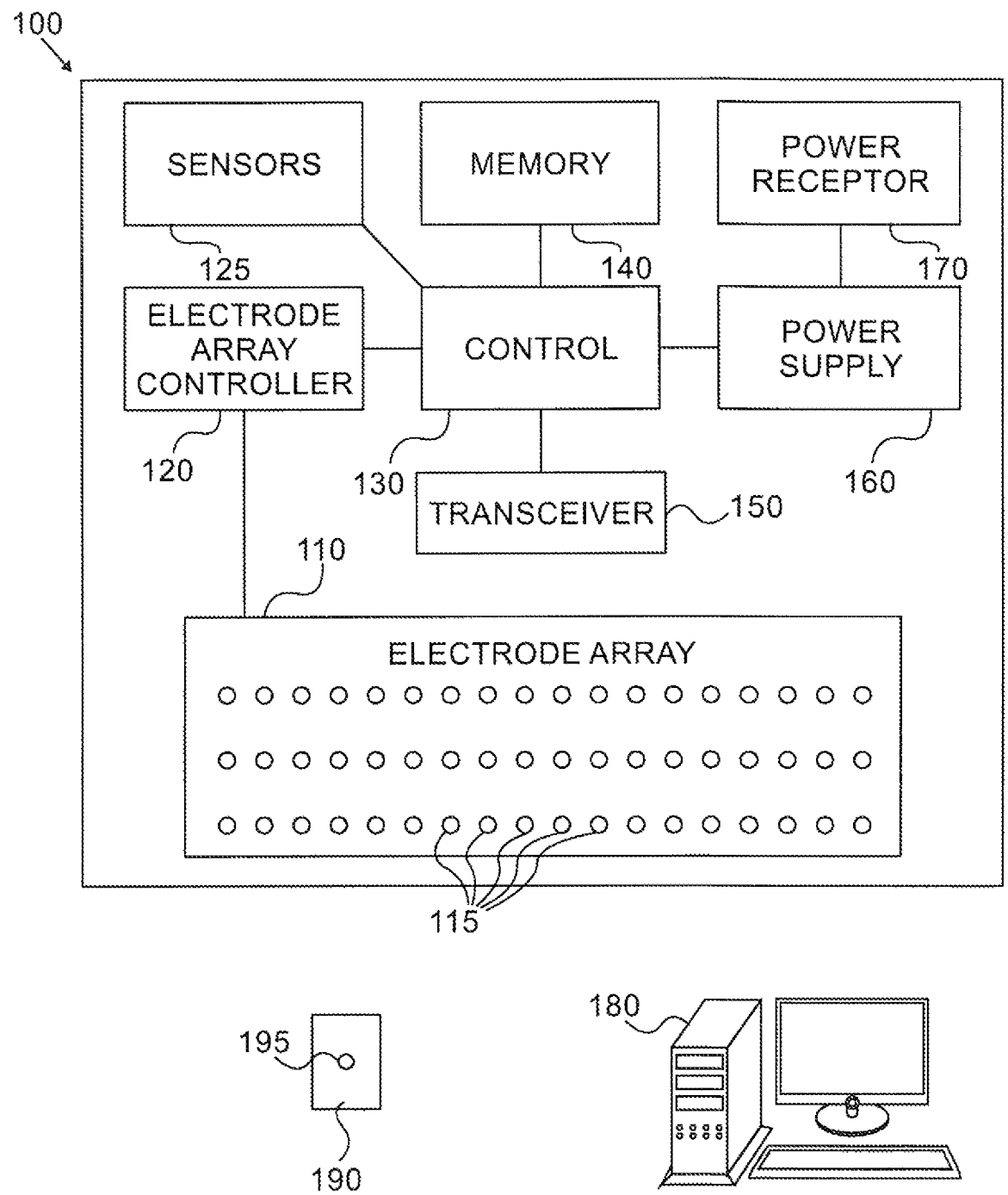
FIG. 1 is a schematic illustration of a block diagram of an electrical stimulator, according to an exemplary embodiment of the invention.

FIG. 1 is a schematic illustration of a block diagram of an electrical stimulator 100, according to an exemplary embodiment of the invention. In an exemplary embodiment of the invention, stimulator 100 includes an electrode array 110, which is designed to be placed in contact with the contact points of nerves or muscles, or in proximity thereof, so that the electrodes can stimulate the contact points. Optionally, the electrode array is denser than the contact points on the muscle or nerve (e.g. 1-100,000 electrodes per millimeter, or per centimeter) or the array of electrodes occupies an area larger than that of the muscle/nerve contact point, so that each contact point on the muscle or nerve that needs to be stimulated will have one or more electrodes 115 in contact with it. In some embodiments of the present invention, some or all of the electrodes can be placed in proximity with the contact points of nerves or muscles. In the context of the present invention placed, includes, but is not limited to implanted, inserted, injected, wrapped, and in any other way positioned in contact or in proximity to contact points of nerves or muscles. In some embodiments of the invention, the tips of the electrodes that are in contact with the patient's tissue may be any shape, for example circular or rectangular. Optionally, the tip may be flat or rounded to prevent electrode array 110 from getting stuck if placed in contact with the patient's tissue before reaching its final position. Alternatively, the tips of the electrode may be coated with materials that encourage tissue fibrosis. Alternatively, the tips may be thorn like to anchor stimulator 100. In an exemplary embodiment of the invention, electrodes 115 are made of or plated with a bio-compatible metal (e.g. a noble metal like platinum or gold).

Optionally, the shape of electrode array 110 is selected based on the type of nerve or muscle needed to be stimulated. In some embodiments of the invention, the shape may be one dimensional (e.g. a line of electrodes), two dimensional or three dimensional.

In an exemplary embodiment of the invention, an electrode array controller 120 is used to control the electrodes 115 of electrode array 110. Optionally, electrode array controller 120 can be used to select or deselect any of the electrodes 115, so that when stimulator 100 outputs a stimulation pulse the selected electrodes will output the pulse. In some embodiments of the invention, some electrodes are output electrodes and some are input electrodes. Alternatively, the electrodes can be selected to be either input or output. Optionally, electrode array controller 120 can use input electrodes as input sensors, for example to serve as an electromyograph (EMG), detecting the resistance/conductivity or action potential of the muscles/nerves in contact with a specific electrode. Optionally, such a measurement can be used to locate the desired area for stimulation of the muscle or nerve and determine which electrodes 115 are in contact with the desired areas.

In an exemplary embodiment of the invention, due to external forces exerted on stimulator 100 after being embedded in a patient, the exact position of the electrode array may shift and electrodes 115 that were previously selected to stimulate contact points may shift over and other electrodes may be in contact with the muscle/nerve contact points in their place. As explained above the electrodes participating in stimulating the muscles/nerves of the patient are dynamically selectable, so that the electrodes 115 participating in stimulating the muscles/nerves can be reselected to overcome such problems.

In an exemplary embodiment of the invention, stimulator 100 includes a control circuit 130, which includes a general purpose CPU or an application specific integrated circuit (ASIC) or the like to control the functionality of the stimulator, for example to determine when to provide a stimulation signal and the parameters of the signal, for example its frequency, pulse width, pulse shape, pulse interval and pulse duration. Optionally, control circuit 130 is preprogrammed to apply various stimulation programs, such as:

1. A nerve stimulation program;
2. A muscle stimulation program; and
3. Biphasic stimulation that alternates polarization on the electrodes 115 to prevent accumulation of ions and acidosis thus reducing tissue damage.

Optionally, each program may use different pulse frequency, shapes, widths, intervals, durations and other parameters for the stimulation signal applied to the electrodes.

In some embodiments of the invention, stimulator 100 includes a memory 140, for example a non-volatile memory that is used to store operational parameters or program code which the control circuit can act upon.

Optionally, stimulator 100 further includes a power supply 160, which may include a rechargeable battery, for example a Li-Ion battery. Alternatively or additionally, the power supply may include a capacitor and/or coil for holding charge for a short term until charging the battery or for immediate consumption. In an exemplary embodiment of the invention, the power for using the device is provided by wireless transmission of power to a power receptor 170, for example an induction coil or RFID coil. In an exemplary embodiment of the invention, stimulator 100 may be activated as long as power receptor 170 is accepting transmitted power. Alternatively, stimulator 100 is first charged and then activated to consume the power from power supply 160. Further alternatively, priority is giving to the stimulation: first stimulating by passing the received power transmission directly to the stimulation circuit, and then charging.

In some embodiments of the invention, stimulator 100 includes a transceiver 150 for communicating between stimulator 100 and an external device, such as a personal computer 180 or an external activation device 190 that is designed to communicate with stimulator 100.

In some embodiments of the invention, the communications and/or power transfer are performed using a non-standard protocol to prevent interference from standard communication equipment. Alternatively, standard communication protocols may be used, for example communicating with WIFI, BlueTooth (BT), RF or other common standards so that stimulator 100 can readily communicate with standard equipment that is readily available, such as personal computer 180 or a cellular telephone (e.g. using BT). Optionally, communications with stimulator 100 may be encrypted and/or require authentication to prevent undesirable transmissions from non-authorized users. Alternatively or additionally, a predefined range of transmission frequencies is used so it will not interfere or receive interference from other radio emitting devices.

In some embodiments of the invention, stimulator 100 includes one or more sensors 125 that sense various parameters such as temperature, sound, vibrations, pressure, electrical current, impedance, and the like. Alternatively or additionally, stimulator 100 receives wireless communication from sensors implanted elsewhere in the patient or located outside of the patient. Optionally, muscle/nerve stimulation can be activated responsive to the measurements of sensors 125. In some embodiments of the invention, stimulator 100 may activate stimulation responsive to specific combinations of measurements. An example of use of an internal or external sensor occurs in dealing with Obstructive Sleep Apnea (OSA). During sleep a person inhales colder air (e.g. at room temperature of about 25° C.) and exhales warmer air (e.g. at body temperature of about 37° C.). Optionally, stimulator 100 may be planted at the base of the tongue adjacent to the air path of the patient's breath. A temperature sensor can follow the breathing pattern by following the temperature changes and alert stimulator 100 to stimulate the tongue muscles responsive to a determination that the tongue is blocking the path. Alternatively, an external sensor can be positioned over the patient's mouth or nose to keep track of the breathing pattern.

In some embodiments of the invention, sensor 125 is used to measure the electrical current or impedance of specific electrodes to determine the importance of the specific electrode in stimulating the nerve/muscle at the current position of stimulator 100 and electrode array 110.

Figure 2A:
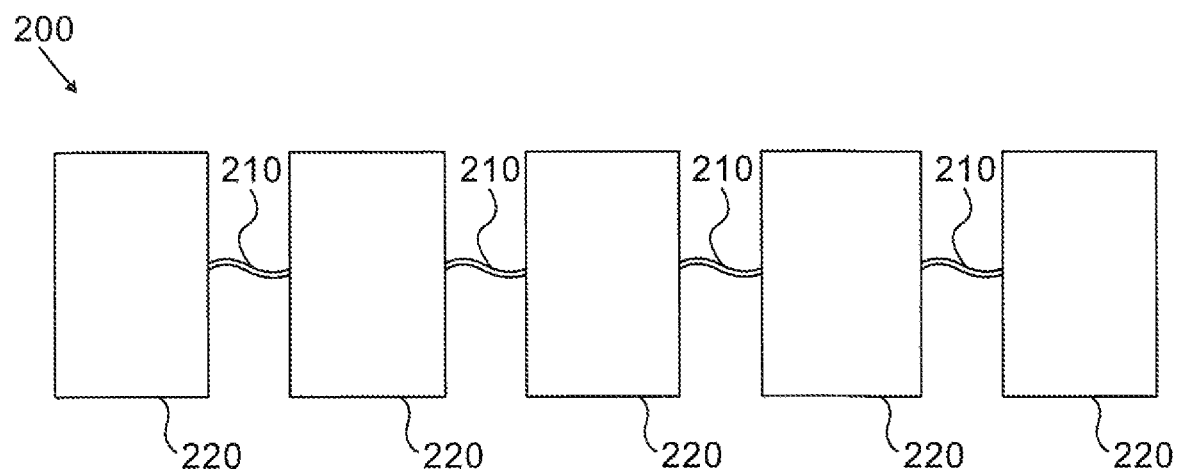
FIG. 2A is a schematic illustration of an electrical stimulator with independent elements connected by flexible wires, according to an exemplary embodiment of the invention.
Figure 2B:
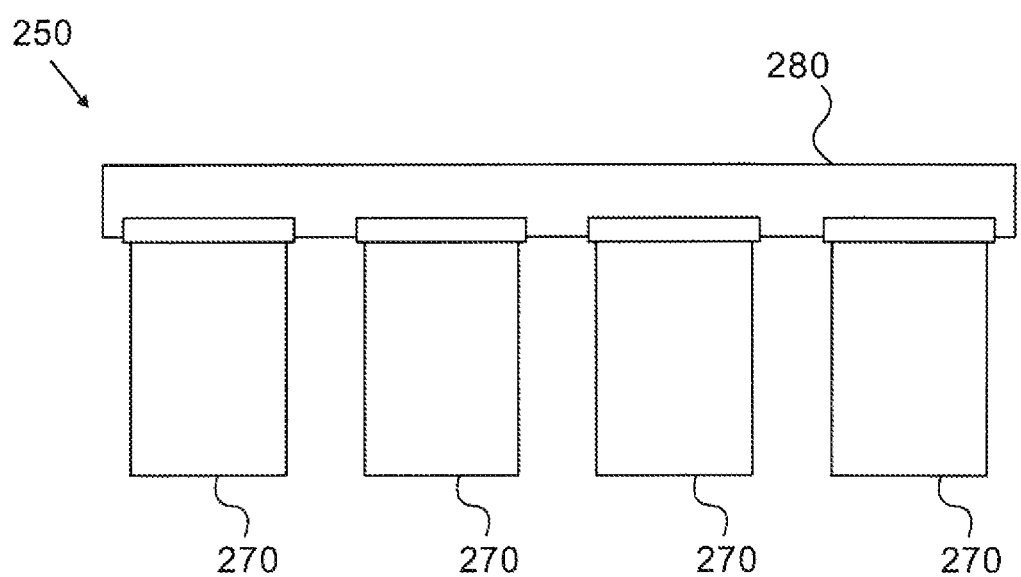
FIG. 2B is a schematic illustration of an electrical stimulator with independent elements connected by a flexible backbone serving as a communication bus, according to an exemplary embodiment of the invention.

FIG. 2A is a schematic illustration of an electrical stimulator 200 with independent elements 220 connected by flexible wires, according to an exemplary embodiment of the invention; and FIG. 2B is a schematic illustration of an electrical stimulator 250 with independent elements 270 connected by a flexible backbone 280 serving as a communication bus, according to an exemplary embodiment of the invention. In an exemplary embodiment of the invention, as illustrated above in FIG. 1 stimulator 100 is made up from various elements. Optionally, each element may comprise a rigid electronic circuit or other rigid parts (e.g. a battery, a coil, a capacitor, an integrated circuit), which communicate electronically with the other elements of stimulator 100. In some embodiments of the invention, as illustrated in FIG. 2A by stimulator 200, elements 220 are electronically connected by flexible wires 210, thus providing a larger overall flexible stimulator 200. Alternatively, as illustrated in FIG. 2B, elements 270 are connected to a flexible communication bus 280, forming an overall flexible stimulator 280. Optionally, a flexible stimulator is less apt to be damaged by external forces and can be more easily manipulated to fit into various positions inside the patient's body. Additionally, a flexible stimulator such as shown in FIG. 2A or 2B will also allow free 3D movement of an organ (e.g. muscle) without causing damage. Optionally, the flexible connection between the elements enables the elements to be freely positioned relative to each other and effectively allow bending or folding of stimulator 100.

Figure 3A:
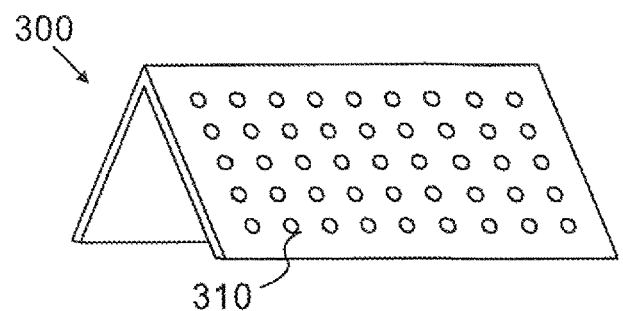
FIG. 3A is a schematic illustration of a flexible electrode array shaped as a tent, according to an exemplary embodiment of the invention.

In an exemplary embodiment of the invention, electrode array 110 is designed to match the muscle or nerve it will be interfacing. FIG. 3A is a schematic illustration of a flexible electrode array 300 shaped as a triangular tent, according to an exemplary embodiment of the invention. In an exemplary embodiment of the invention, the flexible electrode array is shaped to fit the nerve or muscle it is to be placed inside or next to. In another exemplary embodiment of the invention, the flexible electrode array is shaped to fit a recess between nerves or tissue, a compartment in muscles or between tissues, or an epimysial surface. Such recess, compartment or surface can naturally occur or be artificially created. Electrode array 300 is densely populated (e.g. between 1×1 to 1000×1000 electrodes 310 per millimeter square or more, or less) and it is designed to be used to stimulate the Genioglossus muscle at the base of the tongue for treatment of Obstructive Sleep Apnea (OSA). It should be noted that the above design is not limiting and other designs can also be used for treatment of OSA.

Figure 3B:
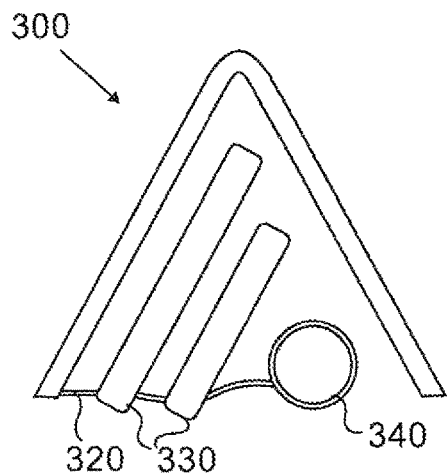
FIG. 3B is a schematic illustration of a flexible electrode array shielding beneath it other elements connected together by a flexible wire, according to an exemplary embodiment of the invention.
Figure 3C:
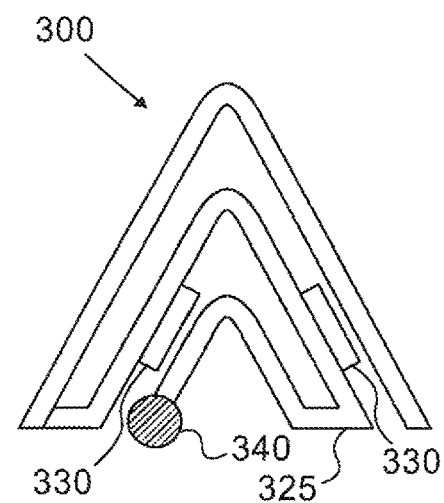
FIG. 3C is a schematic illustration of a flexible electrode array shielding beneath it other elements connected together by a flexible communication bus, according to an exemplary embodiment of the invention.

FIG. 3B is a schematic illustration of a flexible electrode array 300 shielding beneath it other elements 330 connected together by a flexible wire 320 and FIG. 3C is a schematic illustration of a flexible electrode array 300 shielding beneath it other elements 330 connected together by a flexible communication bus 325, according to an exemplary embodiment of the invention; In other exemplary embodiments of the invention, the flexible electrode array can comprise a shape forming a housing, or be placed on a housing, said other elements 330 connected together are placed within said housing.

In an exemplary embodiment of the invention, electrode array 300 is connected by flexible wires 320, as shown in FIG. 3B, to elements 330 and battery 340, which constitute the elements of stimulator 100. Alternatively, electrode array 300 is connected by flexible bus 325, as shown in FIG. 3C, to elements 330 and battery 340, which constitute the elements of stimulator 100. In some embodiments of the invention, battery 340 is not part of the elements of simulator 100. Alternative power sources to battery 340 can include a capacitor, super capacitor, piezo-electric charging material, mechanical (induced by body or other organ or tissue movement) or chemical (such as ionic difference) power sources, coil or a coil having a ferrite core, and the like. In one exemplary embodiment of the invention action potential generated by neurons and nerve tissue across the nerve or muscle are gather via the electrode array and stored in a capacitor (not shown). The action potential translated into energy can be used to power the device of the invention.

In an exemplary embodiment of the invention the housing is made of flexible bio compatible material such that the entire device is flexible.

The triangular tent shape of array 300 and the other shapes disclosed herein, assists in forming contact between electrodes 310 and the contact points at the base of the Genioglossus muscle, or more specifically near the compartments of the Genioglossus oblique fibers, and above the Geniohyoid muscle. Additionally, the triangular tent shape provide for a cavity or an opening underneath thereof that can be exploited to store other elements 330 and battery 340 or other power sources of stimulator 100 by folding them up or placing them beneath array 300 or within said housing (not shown).

Figure 3D:
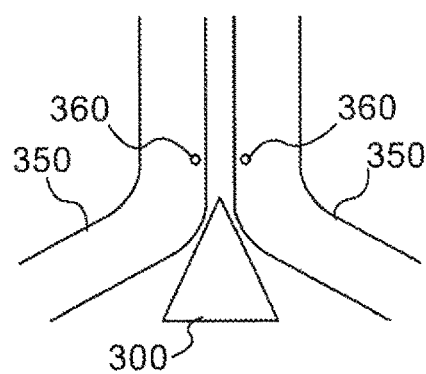
FIG. 3D is a schematic illustration of a flexible electrode array implanted at the base of the tongue, according to an exemplary embodiment of the invention.
Figure 4A:
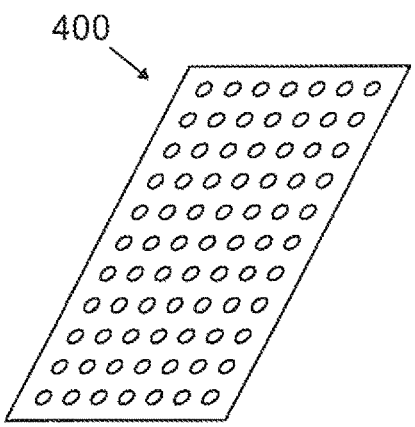
FIG. 4A is a schematic illustration of a flexible electrode array shaped as a flat surface, according to an exemplary embodiment of the invention.
Figure 4B:
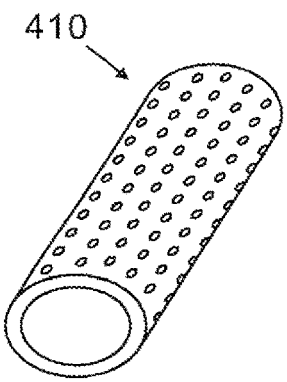
FIG. 4B is a schematic illustration of a flexible electrode array shaped as a cylinder, according to an exemplary embodiment of the invention.
Figure 4C:
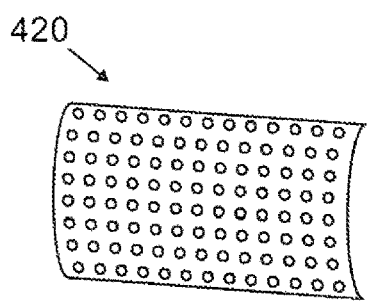
FIG. 4C is a schematic illustration of a flexible electrode array shaped as a 3 dimensional curved surface with electrodes on the inner side, according to an exemplary embodiment of the invention.
Figure 4D:
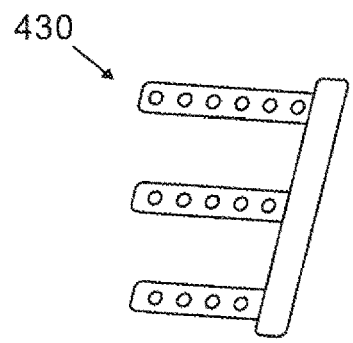
FIG. 4D is a schematic illustration of a flexible electrode array with branches of electrodes extending from a common center, according to an exemplary embodiment of the invention.
Figure 4E:
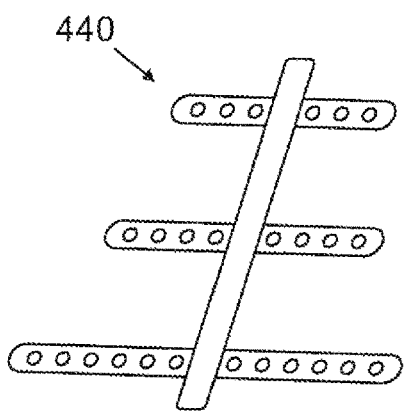
FIG. 4E is a schematic illustration of a flexible electrode array with branches of electrodes of various sizes extending from a common center, according to an exemplary embodiment of the invention.

FIG. 3D is a schematic illustration of flexible electrode array 300 implanted at the base of the tongue, according to an exemplary embodiment of the invention. Optionally, electrode array 300 is designed so that when it is deployed, electrodes 310 will be in contact with the Genioglossus muscle 350 and more specifically adjacent to the Genioglossus horizontal fibers 350 and/or near the Hypoglossal nerves 360, so that electrodes 310 will successfully be able to stimulate the Genioglossus horizontal compartment causing dilation of the pharynx during breathing. Optionally, the shape of electrode array 300 is especially efficient in stimulating the Genioglossus muscle 350, as this muscle has numerous motor end plates, located in various locations in contrast to many other muscles.

FIGS. 4A-4E provide various exemplary shapes of electrode arrays to be used to position the electrode array in proximity with the muscles or nerves that are to be stimulated by the electrodes of the array. The exemplary shapes include:

1. A flat surface 400;
2. A cylinder 410;
3. A 3 dimensional curved surface 420 with electrodes on the inner side to match a cylindrical muscle/nerve;
4. A flexible electrode pad 430 with branches of electrodes extending from a common center; and
5. A flexible electrode pad 440 with branches of electrodes of various sizes extending from a common center.

Optionally, other shapes may be used to maximize contact between the electrodes and the muscles/nerves. In an exemplary embodiment of the invention, the shape is designed to match the muscles/nerves that stimulator 100 is designed to stimulate.

Figure 5:
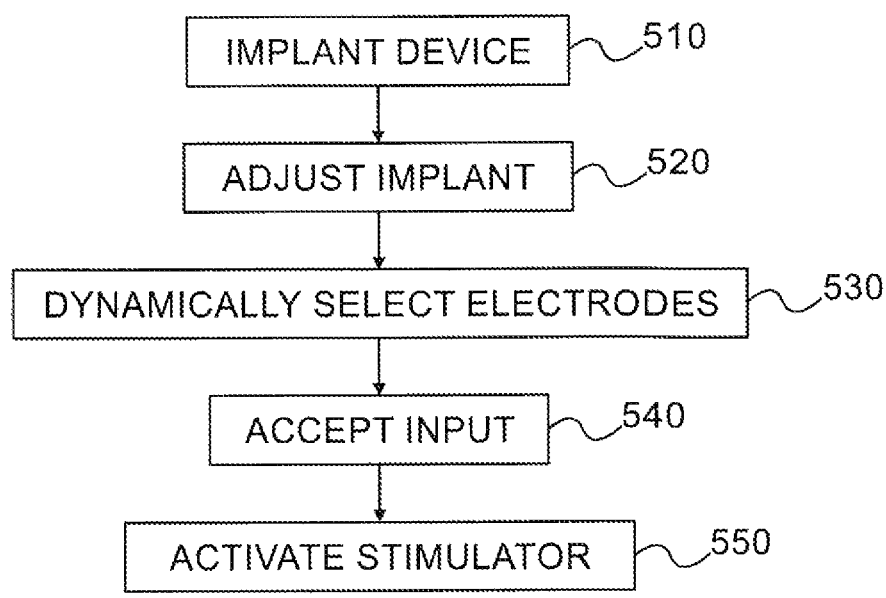
FIG. 5 is a flow diagram of a method of using a stimulator, according to an exemplary embodiment of the invention.

FIG. 5 is a flow diagram 500 of a method of stimulating muscles or nerves using implantable stimulator 100 with an array of electrodes, according to an exemplary embodiment of the invention. In an exemplary embodiment of the invention, a medical practitioner implants (510) the device. The implantation process depends on the location and type of muscle/nerve to be stimulated. Optionally, due to the small size of stimulator 100 (e.g. with a length and width between 0.01 mm to 10 mm) a non-invasive procedure is preferable, for example by injecting the device using a hypodermic needle with local anesthesia only. Optionally, the use of a point and shoot insertion method is preferable, since it is more comfortable for the patient and less invasive. Optionally according to the present invention, stimulator 100 is advantageous since the multiplicity of electrodes relative to the number of contact points on the muscle/nerve and the ability to select the optimal electrodes for stimulation after implantation, reduce the need to adjust the position of stimulator 100 responsive to actual stimulation during the insertion process. An example of use of a stimulator 100 is in dealing with Obstructive Sleep Apnea patients. In an exemplary embodiment of the invention, stimulator 100 is implanted in the vicinity of the Hypoglossal nerve using a shallow transcutaneous approach. In other cases stimulator 100 is implanted into the Genioglossus muscle using an intraoral or transcutaneous/submandibular approach.

Optionally, after implanting stimulator 100 the practitioner may adjust (520) the implanted stimulator responsive to an Ultrasound, MRI, CT, X-ray or other measurements before activating the stimulator 100. In some embodiments of the invention, the implantation is performed using a point and shoot process that does not require additional adjustments, however in some cases, usually depending on the type of stimulator and position of implantation in the patient's body further measurements may be required to verify accurate positioning, and further adjustments may be needed. In some embodiments of the invention, the implantation procedure is performed while using an imaging device (such as Ultrasound, MRI, CT, or X-ray) to guide the practitioner in locating the exact implantation site.

Once stimulator 100 is positioned the electrode array controller 120 dynamically selects (530) the electrodes from electrode array 110 that will be used to stimulate the muscle/nerve.

In some embodiments of the invention, the selection is performed manually by the practitioner, for example by communicating with stimulator 100 (e.g. with computer 180) and either instructing stimulator 100 to activate single electrodes or groups of electrodes while observing the response, and/or instructing stimulator 100 to use the electrode array 110 to measure electrical parameters such as resistance, conductance, or EMG signals, for each electrode or for groups of electrodes. Optionally, the practitioner may also measure a response via an external device, for example a surface EMG, fiber optic, manometer, polysomnograph, pulse oximeter, EEG, microphone.

In some embodiments of the invention, the selection may be performed automatically by electrode array controller 120, wherein electrode array controller 120 measures EMG signals, or other signals, and dynamically selects (530) the electrodes that will participate in the stimulation process responsive to the measurements.

In some embodiments of the invention, stimulator 100 automatically, repeats the dynamic selection process before every use, or periodically (e.g. every day or every week or before the next use, or at predetermined intervals) to verify that stimulator 100 has not moved and to remedy the situation if it has. Such predetermined intervals can be determined through a preprogrammed plan or reprogrammed when so required, or ad hoc as per each use. For example, the dynamic selection can be performed every few seconds or every few minutes or on an hourly basis and the like.

In some embodiments of the invention, stimulator 100 is activated (550) responsive to various inputs accepted (540) by stimulator 100. Optionally, the inputs may be based on physiological parameters of the patient or may be based on commands from an external source such as external activation device 190. In an exemplary embodiment of the invention, external activation device 190 is used to activate the stimulator whenever the patient feels the need, for example when suffering pain or when interested that muscles controlled by stimulator 100 be activated.

Optionally, when treating OSA, the patient may activate stimulator 100 when going to sleep, and stimulator 100 will perform muscle/nerve stimulation responsive to sensors that determine that the patient's tongue needs to be stimulated to enable the patient to breathe. Optionally, external activation device 190 may be a simple transmitter with one or more buttons or switches 195 to transmit signals to stimulator 100 and to select from a few options, for example to stimulate immediately, periodically or responsive to sensor measurements. Alternatively a general purpose computer 180 can be used to program stimulator 100 by transmitting simple or complex commands and receiving responses from stimulator 100. In some embodiments of the invention, external activation device 190 supplies power to stimulator 100. Optionally, stimulator 100 may be activated (550) whenever power is provided. Alternatively, it may charge power supply 160 and be activated (550) at a later time.

In some embodiments of the invention, stimulator 100 may sense various physiological parameters of the patient with sensors 125, for example:

1. Specific periodic vibrations or lack of vibrations from the patient's respiratory system;

2. Temperature in the vicinity of stimulator 100, for example a higher temperature value responsive to the patient expiration in the vicinity of the implanted stimulator 100 and a lower temperature value responsive to the patient inspiration in the vicinity of stimulator 100. A decrease in the temperature change may indicate reduction in breathing;

3. Audio signals, for example, keeping track of the patient's heartbeat, breathing/snoring pattern, or breathing/snoring sounds. Optionally, a decrease in the volume of breathing sounds may indicate an OSA event;

4. EMG signals, for example, keeping track of the patient's muscle tone. Optionally, a decrease in the patient's muscle tone may indicate an OSA event. Optionally, an increase in the patient's respiratory auxiliary muscle tone may indicate an OSA event.

In some embodiments of the invention, sensors are placed at other positions on the patient's body and they communicate wirelessly with stimulator 100.

In some embodiments of the invention, control 130 may perform a pre-programmed algorithm to weigh the results from various inputs and determine if to stimulate or not. Optionally, control 130 can be programmed to decide the specific stimulation protocol (e.g. pulse width, pulse amplitude, pulse shape).

In some embodiments of the invention, stimulator 100 operates independently, without receiving any feedback. Optionally, stimulator 100 is pre-programmed to stimulate at specific times, for specific time duration, or to stimulate periodically, for example for 10 seconds every hour.

It should be appreciated that the above described methods and apparatus may be varied in many ways, including omitting or adding steps, changing the order of steps and the type of devices used. It should be appreciated that different features may be combined in different ways. In particular, not all the features shown above in a particular embodiment are necessary in every embodiment of the invention. Further combinations of the above features are also considered to be within the scope of some embodiments of the invention.

It will be appreciated by persons skilled in the art that the present invention is not limited to what has been particularly shown and described hereinabove. Rather the scope of the present invention is defined only by the claims, which follow.

I claim:

1. An external device configured for location outside of a body of a subject, the external device comprising:
   a switch configured to select a mode from a plurality of stimulation modes, the plurality of stimulation modes including stimulating immediately, stimulating periodically, and stimulating responsive to measurements made by an implantable stimulator, wherein the external device is further configured to:
   receive, from the implantable stimulator, a measurement of an electromyography signal;
   transmit, to the implantable stimulator, a command to dynamically select one or more electrodes within an array of electrodes to stimulate at least one nerve, the one or more electrodes being selected based on the measurement in order to stimulate a desired area of the at least one nerve; and
   wirelessly transmit, to the implantable stimulator, power used both to activate the selected electrodes and to stimulate the at least one nerve, wherein at least some of the power is passed directly to a stimulation circuit of the implantable stimulator for causing nerve stimulation.

2. The device of claim 1, wherein the power for activating the selected electrodes is transmitted for causing a muscle contraction.

3. The device of claim 2, wherein the implantable stimulator is located in a vicinity of the subject's tongue; and
   the power for activating the selected electrodes is transmitted to cause a contraction of a genioglossus muscle of the subject.

4. The device of claim 3, wherein the power for activating the selected electrodes is transmitted to further cause dilation of a pharynx.

5. The device of claim 1, wherein the external device is further configured to transmit stimulation signals to the implantable stimulator.

6. The device of claim 1, wherein the external device is a transmitter configured to wirelessly transmit power to the implantable stimulator.

7. The device of claim 1, wherein external device is further configured to send a command to the implantable stimulator and to receive responses from the implantable stimulator.

8. The device of claim 1, wherein the measurements received from the implantable stimulator are indicative of a sleep-apnea related event.

9. The device of claim 1, wherein the measurements received from the implantable stimulator are indicative of a precursor to a sleep-apnea related event.

10. The device of claim 1, wherein the selected electrodes are activated whenever power is provided.

* * * * *